United States Patent
Hoffmann et al.

(10) Patent No.: US 7,728,171 B2
(45) Date of Patent: *Jun. 1, 2010

(54) PROCESS FOR THE PRODUCTION OF ACID CHLORIDES

(75) Inventors: Ursula Hoffmann, Muttenz (CH); Goesta Rimmler, Bad Krozingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/197,356

(22) Filed: Aug. 25, 2008

(65) Prior Publication Data

US 2009/0036703 A1  Feb. 5, 2009

Related U.S. Application Data

(63) Continuation of application No. 11/582,000, filed on Oct. 17, 2006, now Pat. No. 7,435,849.

(30) Foreign Application Priority Data

Oct. 31, 2005  (EP)  .................. 05110177

(51) Int. Cl.
C07C 51/60  (2006.01)
(52) U.S. Cl. ..................... 562/856; 562/862; 564/154; 564/189; 564/190
(58) Field of Classification Search ................. 562/856, 562/862; 564/154, 189, 190
See application file for complete search history.

(56) References Cited

U.S. PATENT DOCUMENTS

| 2,899,458 | A | 8/1959 | Wilson |
| 4,129,595 | A | 12/1978 | Suzuki |
| 7,435,849 | B2 * | 10/2008 | Hoffmann et al. ........... 562/856 |

FOREIGN PATENT DOCUMENTS

EP  1 020 439  7/2000
WO  WO 2004/056752 A1  7/2004

OTHER PUBLICATIONS

Shinkai et al., J. Med. Chem., 43, pp. 3566-3572 (2000).
Hauser, Mal, Journal of the American Chemical Society, vol. 105, pp. 5688-5690 (1983), XP002416563.

* cited by examiner

*Primary Examiner*—Shailendra Kumar
(74) *Attorney, Agent, or Firm*—George W. Johnston; Dennis P. Tramaloni; Brian C. Remy

(57) ABSTRACT

A process for the preparation of acid halides of formula I

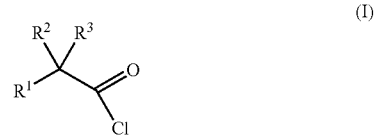

(I)

which are useful as intermediates in the preparation of i.a. pharmaceutically active compounds.

13 Claims, No Drawings

PROCESS FOR THE PRODUCTION OF ACID CHLORIDES

PRIORITY TO RELATED APPLICATIONS

This application is a continuation of application Ser. No. 11/582,999, filed Oct. 17, 2006, now U.S. Pat. No. 7,435,849, which claims the benefit of European Application No. 05110177.2, filed Oct. 31, 2005. The entire contents of the above-identified applications are hereby incorporated by reference.

The present invention is directed to a process for the preparation of acid halides which are useful as intermediates in the preparation of i.a. pharmaceutically active compounds.

In one aspect the present invention provides a process for the preparation of a compound of formula I

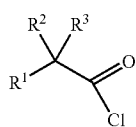

(I)

wherein $R^1$ is hydrogen, $C_1$-$C_8$alkyl or $C_2$-$C_8$alkenyl which are unsubstituted or substituted by one or more substituents selected from $C_1$-$C_8$alkoxy and $C_3$-$C_8$cycloalkyl; and $R^2$ and $R^3$ together are $C_3$-alkylenyl or $C_3$-alkenylenyl;

comprising reacting a compound of formula II

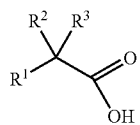

(II)

wherein $R^1$, $R^2$ and $R^3$ have the above meanings;

with thionylchloride in the presence of a tri-$C_1$-$C_5$alkylamine.

In another aspect the present invention provides a process for the preparation of a compound of formula I

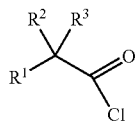

(I)

wherein $R^1$ is hydrogen, $C_1$-$C_8$alkyl or $C_2$-$C_8$alkenyl which are unsubstituted or substituted by one or more substituents selected from $C_1$-$C_8$alkoxy and $C_3$-$C_8$cycloalkyl; and $R^2$ and $R^3$ are combined with the carbon atom to which they are attached to form $C_3$-$C_7$cycloalkyl or $C_5$-$C_8$cycloalkenyl;

comprising reacting a compound of formula II

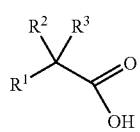

(II)

wherein $R^1$, $R^2$ and $R^3$ have the above meanings;

with thionylchloride in the presence of a tri-$C_1$-$C_5$alkylamine.

The compounds of formula I may be used as intermediates in the synthesis of valuable pharmaceutical compounds, e.g. those as described in e.g. EP 1,020,439.

Accordingly, in another embodiment the present invention provides a process comprising the synthetic steps represented in the following scheme:

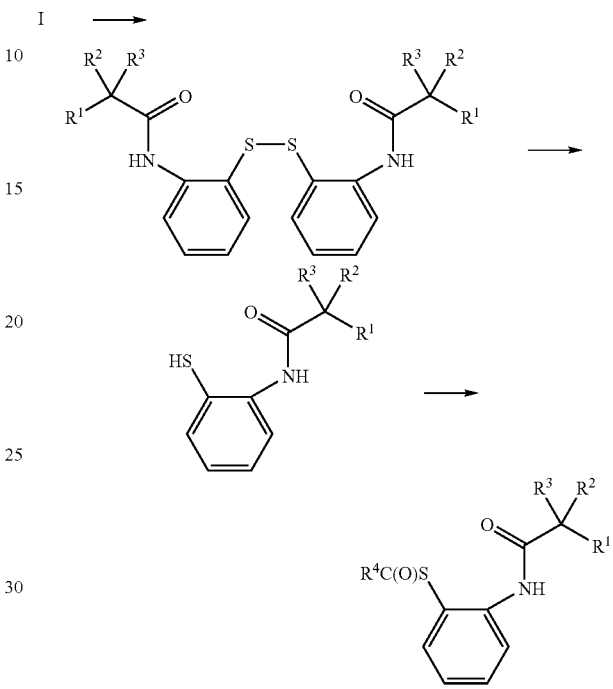

wherein $R^1$, $R^2$ and $R^3$ are as defined above and $R^4$ is $C_1$-$C_8$alkyl. In particular, the process comprises reacting a compound of formula I with bis(2-aminophenyl)disulfide to acylate the amino groups of the (2-aminophenyl)disulfide, reducing the amino-acylated disulfide product with a reducing agent such as triphenylphosphine, zinc or sodium borohydride to yield the thiol product, and acylating the thiol group in the thiol product with $R^4C(O)Cl$.

The additional steps may be performed, e.g., according to the procedures described in Shinkai et al., J. Med. Chem. 43:3566-3572 (2000).

Examples for $C_1$-$C_8$alkyl include methyl, ethyl, straight and branched propyl, butyl, pentyl, hexyl, e.g. $CH_2CH(CH_2CH_3)_2$, heptyl and octyl. For $R^1$, $C_1$-$C_8$alkyl is preferably $CH_2CH(CH_2CH_3)_2$. For $R^4$, $C_1$-$C_8$alkyl is preferably isopropyl.

Examples for $C_2$-$C_8$alkenyl include unsaturated carbon chains containing one or more double bonds at any possible position, e.g. vinyl, allyl, butenyl, pentenyl, hexenyl, heptenyl and octenyl.

Examples for $C_3$-$C_7$cycloalkyl include cyclopropyl, cyclobutyl, cyclopentyl, cyclohexyl and cycloheptyl. Preferred is e.g. cyclohexyl. Examples for $C_5$-$C_8$cycloalkenyl include cyclopentenyl, cyclohexenyl, cycloheptenyl, cyclooctenyl, cyclopentadienyl, cyclohexadienyl, cycloheptadienyl and cyclooctadienyl. Preferred are cyclopentenyl, cyclohexenyl and cycloheptenyl.

The term "tri-$C_1$-$C_5$alkylamine" denotes a compound of formula $R^4N(R^5)R^6$ wherein $R^4$, $R^5$ and $R^6$ independently are a $C_1$-$C_8$alkyl, and includes triethylamine, tributylamine, diethyl-methylamine, dimethyl-ethylamine and methylethyl-butylamine. The process may take place at a temperature in the range from 20 to 60° C., e.g. in a range from 40 to 55° C.

The process may be performed without a solvent or in the presence of a solvent, e.g. in the presence of an aromatic or chlorinated solvent, e.g. in the presence of methylene chloride, chloroform, toluene or benzene, e.g. in the presence of toluene.

The acylating steps of the present invention are preferably conducted in the presence of a base. Preferred bases include organic bases with pyridine being a preferred organic base.

The amount of thionylchloride in relation to the compound of formula I in the reaction mixture may be in the range from 1.0 to 2.0 equivalents of thionylchloride, e.g. from 1.0 to 1.2 equivalents, e.g. 1.2 equivalents.

The amount of the tri-$C_1$-$C_5$alkylamine in relation to the amount of the compound of formula I may be at a ratio of from 5 mol % to 0.1 mol %, e.g. from 0.3 mol % to 0.5 mol %, e.g. 0.3 mol %.

In another aspect the present invention provides a process for the preparation of a compound of formula I as above, comprising reacting a compound of formula II as above in the presence of a tri-$C_1$-$C_5$alkylamine by continuously adding thionylchloride.

The term "continuously adding" denotes the addition of thionylchloride to a solution of compound I and optionally a solvent during a period of time from 10 minutes to 5 hours, depending on the batch size. The solution of compound I and optionally a solvent is heated to the desired temperature prior to the addition of thionylchloride. This method is different from the batch mode where all components are mixed at RT and the mixture is heated to the desired temperature.

In one embodiment the present invention provides a process for the preparation of a compound of formula I wherein $R^1$ is —$CH_2CH(CH_2CH_3)_2$. In another embodiment the present invention provides a process for the preparation of a compound of formula I wherein the tri-$C_1$-$C_5$alkylamine is triethylamine or tributylamine. In still another embodiment the present invention provides a process for the preparation of a compound of formula I wherein the tri-$C_1$-$C_5$alkylamine is tributylamine.

The compounds of formula II are commercially available or can be prepared by procedures known to the skilled person.

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom.

EXAMPLE 1

Preparation of
1-(2-Ethyl-butyl)-cyclohexanecarbonyl Chloride in the Absence of a Catalyst A mixture of 103.0 mmol 1-(2-ethyl-butyl)-cyclohexanecarboxylic acid and 38.9 mmol cyclohexanecarboxylic acid was warmed to 50° C. 12.4 mL (170.3 mmol=1.2 Eq. relative to the sum of both acids) of thionyl chloride was added during 16 minutes at a temperature of 44-50° C. (reaction is endothermic) and the reaction mixture was kept at 52-53° C. After 1 hr the reaction was incomplete (5.2% 1-(2-ethyl-butyl)-cyclohexanecarboxylic acid and 13.8% 1-(2-ethyl-butyl)-cyclohexanecarboxylic acid anhydride), after 6 hrs still incomplete (1.9% 1-(2-ethyl-butyl)-cyclohexanecarboxylic acid and 2.8% 1-(2-ethyl-butyl)-cyclohexanecarboxylic acid anhydride). After addition of another 4.0 mL (55 mmol) thionylchloride and 3 hr at 52-53° C. the reaction was almost complete (0.18% 1-(2-ethyl-butyl)-cyclohexanecarboxylic acid and 0.47% 1-(2-ethyl-butyl)-cyclohexanecarboxylic acid anhydride). After removing volatile components in vacuo (60° C. bath, 3.3-3.7 mbar followed by 120° C. bath, 9.3-9.6 mbar) 20.21 g of residue was obtained (assay 96.6% 1-(2-ethyl-butyl)-cyclohexanecarbonyl chloride, yield 82.1%).

EXAMPLE 2

Preparation of
1-(2-Ethyl-butyl)-cyclohexanecarbonyl chloride in the presence of 0.02 Eq. triethylamine A mixture of 103.0 mmol 1-(2-ethyl-butyl)-cyclohexanecarboxylic acid, 38.9 mmol cyclo-hexanecarboxylic acid and 396 µL triethylamine (2.84 mmol=0.02 eq. relative to the sum of both acids) was warmed to 50° C. 12.4 mL (170.3 mmol=1.2 Eq. relative to the sum of both acids) of thionyl chloride was added during 18 minutes at a temperature of 40-54° C. (reaction is endothermic, vigorous gas evolution) and the reaction mixture was kept at 54-55° C. After 1 hr reaction was complete (0.03% 1-(2-ethyl-butyl)-cyclohexanecarboxylic acid and no 1-(2-ethyl-butyl)-cyclohexanecarboxylic acid anhydride). After removing volatile components in vacuo (60° C. bath, 3.5-4.3 mbar followed by 120° C. bath, 10-11 mbar) 25.44 g of residue was obtained (assay 92.9% 1-(2-ethyl-butyl)-cyclohexanecarbonyl chloride, yield 99.4%).

EXAMPLE 3

Preparation of
1-(2-Ethyl-butyl)-cyclohexanecarbonyl Chloride in the Presence of 0.005 Eq. Triethylamine A mixture of 103.0 mmol 1-(2-ethyl-butyl)-cyclohexanecarboxylic acid, 38.9 mmol cyclo-hexanecarboxylic acid and 100 µL triethylamine (0.72 mmol=0.005 eq. relative to the sum of both acids) was warmed to 50° C. 12.4 mL (170.3 mmol=1.2 Eq. relative to the sum of both acids) of thionyl chloride was added during 22 minutes at a temperature of 41-51° C. (reaction is endothermic, vigorous gas evolution) and the reaction mixture was kept at 54-55° C. After 10 minutes the reaction was almost complete (0.13% 1-(2-ethyl-butyl)-cyclohexanecarboxylic acid and 0.13% 1-(2-ethyl-butyl)-cyclohexanecarboxylic acid anhydride). After 1.5 hr the reaction was complete (0.04% 1-(2-ethyl-butyl)-cyclohexanecarboxylic acid and no 1-(2-ethyl-butyl)-cyclohexanecarboxylic acid anhydride). After removing volatile components in vacuo (60° C. bath, 3.5-4.3 mbar followed by 120° C. bath, 10-11 mbar) 26.19 g of residue was obtained (assay 92.9% 1-(2-ethyl-butyl)-cyclohexanecarbonyl chloride, yield 100%).

EXAMPLE 4

Preparation of
1-(2-Ethyl-butyl)-cyclohexanecarbonyl Chloride in the Presence of 0.005 Eq. Tributylamine A mixture of 103.0 mmol 1-(2-ethyl-butyl)-cyclohexanecarboxylic acid, 38.9 mmol cyclo-hexanecarboxylic acid and 173 µL tributylamine (0.71 mmol=0.005 eq. relative to the sum of both acids) was warmed to 50° C. 12.4 mL (170.3 mmol=1.2 Eq. relative to the sum of both acids) of thionyl chloride was added during 16 minutes at a temperature of 44-51° C. (reaction is endothermic, vigorous gas evolution) and the reaction mixture was kept at 53-55° C. After 15 minutes the reaction was complete (0.08% 1-(2-ethyl-butyl)-cyclohexanecarboxylic acid and no 1-(2-ethyl-butyl)-cyclohexanecarboxylic acid anhydride). After removing volatile components in vacuo (60° C. bath, 2.7-1.9 mbar followed by 120° C. bath, 8.8-13 mbar) 24.86 g of the residue was obtained (assay 95.8% 1-(2-ethyl-butyl)-cyclohexanecarbonyl chloride, yield 100%).

The invention claimed is:

1. A process for the preparation of a compound of formula I:

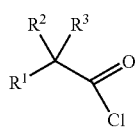

(I)

wherein
R$^1$ is hydrogen, C$_1$-C$_8$alkyl or C$_2$-C$_8$alkenyl which are unsubstituted or substituted by one or more substituents selected from C$_1$-C$_8$alkoxy and C$_3$-C$_8$cycloalkyl; and R$^1$ and R$^3$ are combined with the carbon atom to which they are attached to form C$_3$-C$_7$ cycloalkyl or C$_5$-C$_8$cycloalkenyl;
comprising reacting a compound of formula II

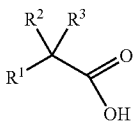

(II)

wherein R$^1$, R$^2$ and R$^3$ have the above meanings; with thionylchloride in the presence of tributylamine.

2. The process according to claim 1 additionally comprising the step of acylating a compound of the formula III

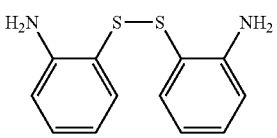

(III)

with a compound of formula I to yield a compound of formula IV

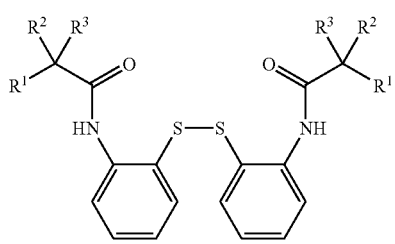

(IV)

wherein R$^1$, R$^2$ and R$^3$ are as defined in claim 1.

3. The process according to claim 2 additionally comprising the step of reducing the compound of formula IV with a reducing agent to yield a compound of formula V

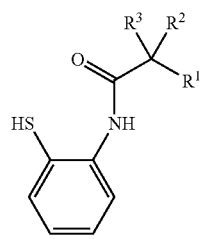

(V)

wherein R$^1$ is hydrogen, C$_1$-C$_8$alkyl or C$_2$-C$_8$alkenyl which are unsubstituted or substituted by one or more substituents selected from C$_1$-C$_8$alkoxy and C$_3$-C$_8$cycloalkyl; and R$^2$ and R$^3$ are combined with the carbon atom to which they are attached to form C$_3$-C$_7$-cycloalkyl or C$_5$-C$_8$cycloalkenyl.

4. The process according to claim 3 additionally comprising the step of acylating the compound of formula V with R$^4$C(O)Cl to yield a compound of formula VI

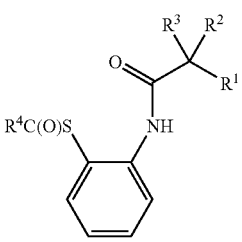

(VI)

wherein R$^1$ is hydrogen, C$_1$-C$_8$alkyl or C$_2$-C$_8$alkenyl which are unsubstituted or substituted by one or more substituents selected from C$_1$-C$_8$alkoxy and C$_3$-C$_8$cycloalkyl; and R$^2$ and R$^3$ are combined with the carbon atom to which they are attached to form C$_3$-C$_7$-cycloalkyl or C$_5$-C$_8$cycloalkenyl and R$^4$ is C$_1$-C$_8$ alkyl.

5. The process according to claim 4 wherein R$^4$ is isopropyl.

6. The process according to claim 1 wherein the thionyl chloride is present in the range from 1.0 to 2.0 equivalents of thionylchloride in relation to the compound of formula I.

7. The process according to claim 1 wherein the amount of the tributylamine in relation to the amount of the compound of formula I is at a ratio of from 5 mol % to 0.1 mol %.

8. The process according to claim 1 wherein in formula I R$^2$ and R$^3$ are combined with the carbon atom to which they are attached to form C$_3$-C$_7$cycloalkyl.

9. The process according to claim 1 wherein in formula I R$^1$ is CH$_2$CH(CH$_2$CH$_3$)$_2$ and R$^2$ and R$^3$ are combined with the carbon atom to which they are attached to form cyclohexyl.

10. The process according to claim 2 wherein the acylating step is performed in the presence of a base.

11. The process according to claim 4 wherein the acylating step is performed in the presence of a base.

12. The process according to claim 10 wherein the base is an organic base.

13. The process according to claim 11 wherein the base is an organic base.

* * * * *

UNITED STATES PATENT AND TRADEMARK OFFICE
CERTIFICATE OF CORRECTION

PATENT NO. : 7,728,171 B2 Page 1 of 1
APPLICATION NO. : 12/197356
DATED : June 1, 2010
INVENTOR(S) : Ursula Hoffmann It is certified that error appears in the above-identified patent and that said Letters Patent is hereby corrected as shown below:

Claim 2, column 5, line 52, delete "formula Ito" and insert -- formula I to --.

Signed and Sealed this

Twentieth Day of July, 2010

David J. Kappos
*Director of the United States Patent and Trademark Office*